United States Patent [19]

Pauwels et al.

[11] Patent Number: 4,845,039

[45] Date of Patent: Jul. 4, 1989

[54] METHOD OF LABELING AMINE-CONTAINING COMPOUNDS WITH A METAL

[75] Inventors: Ernest K. J. Pauwels; Rolf I. J. Feitsma, both of Leiden, Netherlands

[73] Assignee: Academisch Ziekenhuis Leiden, Leiden, Netherlands

[21] Appl. No.: 890,780

[22] PCT Filed: Nov. 14, 1985

[86] PCT No.: PCT/NL85/00045

§ 371 Date: Jul. 10, 1986

§ 102(e) Date: Jul. 10, 1986

[87] PCT Pub. No.: WO86/03010

PCT Pub. Date: May 22, 1986

[30] Foreign Application Priority Data

Nov. 15, 1984 [NL] Netherlands ............ 8403494

[51] Int. Cl.$^4$ ............................................. G01N 33/53
[52] U.S. Cl. ........................... 436/548; 436/545; 436/804; 424/1.1; 530/389; 530/402; 534/10
[58] Field of Search ............ 436/548, 804, 545; 530/402, 389; 424/1.1; 534/10

[56] References Cited

U.S. PATENT DOCUMENTS 4,238,589 12/1980 Cleeland, Jr. et al. ............ 546/239
4,472,509 9/1984 Garison et al. .................... 435/548

*Primary Examiner*—Robert J. Warden
*Assistant Examiner*—Stephen C. Wieder
*Attorney, Agent, or Firm*—Hamilton, Brook, Smith & Reynolds

[57] ABSTRACT

Method for labelling amine-containing compounds like proteins with a metal, particularly technetium-99m comprising reacting metal ions in an acidic medium with a compound represented by formulae (I) or (II), wherein $R_1$, $R_2$ and $R_3$ are independently selected from hydrogen, alkyl, substituted alkyl, aryl, alkanyl etc. to form a reactive intermediate compound and thereafter reacting said reactive intermediate compound with the amine-containing compound to be labeled. This kind of labeled amine-containing compounds have beneficial properties in immuno-diagnostic and therapeutic applications, particularly when they are used in vivo.

13 Claims, No Drawings

METHOD OF LABELING AMINE-CONTAINING COMPOUNDS WITH A METAL

FIELD OF THE INVENTION

This invention is in the field of chemistry and particulary relates to the labeling of amine-containing compounds, such as proteins, with metals.

BACKGROUND OF THE INVENTION

Proteins are used widely in bio-medical science. For example, antibodies are particularly useful in many diagnostic or therapeutic applications because of their special biological activity and their specific affinity for certain antigenic determinants found on specialized cells in tissue and organs.

The ability to detect the extent to which an antibody has accumulated within certain tissue or organs often depends upon the detection of a label bound to the antibody. Labels which emit radioactivity, fluorescent light under excitation or signals detectible by NMR measurements have been employed.

Although certain metal radioisotopes have been employed as labels, there have been limitations on such use to date. For example, the methods heretofore available for labeling proteins with metal radioisotopes have been of limited utility and have been limited to specific metals. A need has existed, for example, for a better method for labeling antibodies, particularly monoclonal antibodies, with technetium-99m ($^{99m}Tc$), a particularly desirable metal radioisotope.

DESCRIPTION OF THE INVENTION

This invention provides a method for labeling proteins and other amine-containing compounds with metals. The method involves reacting metal ions in an acidic medium with a compound represented by the formulas:

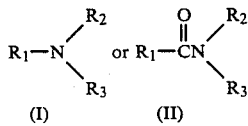

wherein $R_1$, $R_2$ and $R_3$ are individually selected from hydrogen, alkyl, substituted alkyl, aryl, alkaryl, etc. An example of an amine compound of formula I is diethylamine. Specific examples of amide compounds of formula II are dimethyl formamide (DMF), diethylformamide and monomethyl formamide. The result of this first reaction is a reactive intermediate compound containing the metal and which is subsequently reacted with the compound to be labeled in a solution having a pH selected for the particular compound being labeled.

This method allows the labeling of proteins with metal radioisotopes to produce labeled proteins having beneficial properties for immuno-diagnostic and therapeutic applications. Labeled proteins can be produced which are non-toxic, non-pyrogenic and sterile. These are important properties, particularly where the labeled protein will be used in vivo. Very importantly, the metal labels are tightly bound to the proteins and do not significantly interfere with the biological activity of the proteins.

This method is particularly suitable for labeling monoclonal antibodies (MAb) with the radioisotope technetium-99m ($^{99m}Tc$). For example, DMF can be employed in a two-step method for labeling MAb with $^{99m}Tc$ by the following procedure. In a first step, DMF is reacted with technetium pertechnetate under acidic conditions for about four hours at a temperature of about 140° C. to form a reactive $^{99m}Tc$ intermediate compound which precipitates as a crystalline white powder. In a second step, the reactive $^{99m}Tc$ compound and MAb are reacted at higher pH (e.g., 7.0) which is maintained with a buffer for about one hour to produce the monoclonal antibody labeled with technetium-99m. This reaction scheme can be illustrated as follows:

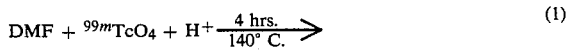

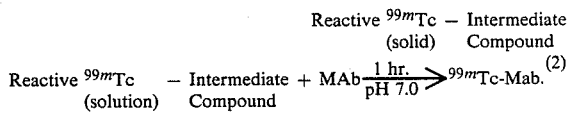

A high yield (e.g., 90%) of the reactive intermediate compound can be obtained by careful selection of the elevated temperature employed in the first reaction. The specific temperature depends, of course, on the specific reactants and other reaction conditions. When using DMF, it has been found that temperatures between about 135° C. and 145° C. are preferred.

The H+ ions required for the desired acidity can be obtained by addition of an acid. Hydrochloric acid is one satisfactory acid in this respect. Good results have been obtained, in particular, by using a ten-fold molecular excess of the amine or amide with respect to HCl.

The pH of the solution which is used in the second reaction stage is chosen as a function of the compound to be labeled. Preferably, the solution is buffered with a buffer which does not contain amine groups which would also react with the reactive intermediate compound and thus compete with the compound being labeled for the reactive intermediate compound.

The method of this invention is of interest in particular for labeling of biologically active proteins with a radionuclide, especially Tc-99m. In nuclear medicine, radioactive substances (radiopharmaceuticals) are administered to patients for human diagnosis. On the basis of a distribution pattern (possibly over time) a diagnosis can be made or a contribution to a diagram can be provided. The distribution pattern in the body is recorded by appropriate instruments which produce images or scintigrams. General requirements of radiopharmaceuticals, in addition to the ones already mentioned with respect to labeled compounds for medical diagnosis, are that the radionuclide have a relatively short half-life, which prevents unnecessary radiation-dose, and that it can be detected with high efficiency.

Radiopharmaceuticals are, in general, biologically active substances which possess a certain affinity for physiological or pathophysiological tissue, or take part in pathophysiological processes. In this respect much attention has always been paid to the use of radioactive proteins as radiopharmaceuticals. This interest has come forward clearly in recent years when monoclonal antibodies appeared to be applicable in nuclear medicine.

Scintigraphic examination by means of proteins has been carried out in the past with radionuclides of iodine. In the "American Heart Journal", No. 105 (1981), pp. 614–618 and in "Radiotherapy and Oncology", No. 1

(1984), pp. 333–338, the use of I-123, I-125 and I-131 is described. The half-lives of the isotopes I-125 and I-131 (60 days and 8 days respectively) make these radionuclides less suitable due to relatively high radiation loads for patients, environment and nuclear medical personnel. For scintigraphic examination, a gamma-photon-energy of 100-200 keV of the radionuclide is also desirable in order to obtain a good image (scintigram) by means of a gamma-camera (I-125 and I-131 do not have such a gamma-photon-energy). The radio-nuclide I-123 ($T_{\frac{1}{2}}=14$ hours, E(gamma)=160 keV) does possess these properties, but this isotope is very expensive, difficult to obtain and often contains radionuclidic impurities.

The use of the radionuclide technetium-99m is known in the nuclear medicine for labeling substances; see for example the "Journal of Nuclear Medicine", No. 11 (1970), p. 147, or more recently, the "Journal of Nuclear Medicine", No. 23 (1982), pp. 1011–1019. Technetium-99m is relatively inexpensive, can be obtained in a simple manner and possesses the relatively short half-life of 6 hours. The photon-energy of this nuclide is 140 keV, but no beta-radiation is emitted, minimizing radiation dose to the patient.

By means of the method according to this invention, it is thus possible to label proteins with a metallic radionuclide with a relatively short half-life, while retaining the biological activity of the protein. In addition, high labeling yields (e.g. 95%) have been obtained, particularly with the use of DMF as described herein.

Although this invention has been described above employing $^{99m}$Tc, other radionuclides can be employed. An example of another is chromium-51 ($^{51}$Cr). Additionally, the invention can be employed to label compounds with metals such as manganese, gadolinium and iron, which metals are useful in nuclear magnetic resonance.

The method of this invention can also be employed in labeling compounds other than proteins with metals. Examples of other amine-containing compounds which can be labeled with metals employing this method are amino acids, nucleotides and amino-containing drugs. Such labeled compounds can have utility in nuclear magnetic resonance imaging, scintigraphy, immunoassays, etc.

The method according to the invention will be illustrated in more specific detail by means of the following examples,

EXAMPLE 1

The reaction of Tc-99m with the protein takes place as follows and under the reaction conditions as indicated:

DMF + $^{99m}$TcO$_4^-$ + HCl 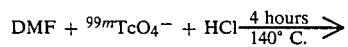 (1)

reactive Tc-99m compound
solid reactive Tc-99m compound + protein 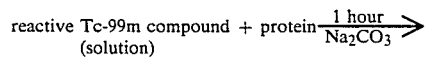 (2)
(solution)

buffer protein labeled with Tc-99m.

The first reaction has been carried out at a temperature of about 140° C.

The following variables were investigated where applicable and optimized:

1. the acidity during both steps of the labeling process;
2. the concentrations of DMF and HCl;
3. the concentration of protein;
4. the reaction temperature;
5. the reaction time.

The TcO$_4^-$ ion is always present in "carrier-free" or trace amounts and is not an important reaction parameter.

A good result wherein more than 95% of the pertechnetate added is retrieved as labeled protein is obtained with 40 microliters DMF and 52 microliters of 1N HCl per millileter of technetium eluant from a molybdenum technetium generator. The use of 0.4 mg DMF per mg protein is customary.

The labeling efficiency of the method carried out was determined by means of:

electrophoresis in 0.1 molar acetate buffer, pH 5.0, 250 V for 4 minutes gel filtration on a column of 10 cm of "Sephadex G50" with 0.9% NaCl as eluant. The elution of the labeled protein takes place in the void column.

precipitation by means of trichloroacetic acid, wherein the labeled protein is precipitated. The product of reaction stage 1 does not precipitate under these conditions.

as determined, for example, by means of autoradiography a (qualitative method to get a first impression of the labeling.

The radiochemical yield was measured in the reactions which are carried out with the proteins fibrinogen, human serum albumin, and a monoclonal antibody against human fibrin and was always more than 95% at temperatures (during the first reaction) between 135° C. and 145° C., and at a time of reaction of at least 4 hours. At other temperatures, the yield decreased: e.g., at 130° C., 90%; at 150° C., 92%. The yield decreased also at times of reaction of less than 4 hours: e.g. at 3 hours 90%; at 2 hours, 30% (reaction temperature always 140° C.). By means of agar electrophoresis of a labeled protein after contact for 4 hours with serum, the technetium labeled protein did not demonstrate disassociation of the label. It was shown that technetium-99m labeling of a mixture of human serum proteins resulted in a uniform labeling of the various proteins.

By established in vivo and in vitro techniques, it was shown that the immunological and biochemical properties of the proteins were not significantly affected.

EXAMPLE 2

Labelling of Human Serum Albumin, Fibrinigen and Anti-Fibrin with Technetium-99m glassware: reaction vial 5 ml. micro-pipets (for instance: Gilson Pipetman).

Apparatus: heater hairblower lead (for radiation protection)

Chemicals: 5N hydrochloric acid N,N-dimethylformamide (Merck nr. 82275) $^{99m}$Tc-pertechnetate eluant protein, highly concentrated in saline Na$_2$Co$_3$ buffer solution 0.05 mol, pH : 8.0 eventually: chloroform (zur Analyse Merck nr. 2445)

Procedure:
(1) add 50 ul N,N-dimethylformamide to 1 ml $^{99m}$Tc-pertechnetate-eluant and add subsequently 14 ul 5 N HCl.
(2) the reaction mixture is heated during 4–5 hours at 140° C. (to be optimized).

(3) white crystalline material (powder) that is present at the bottom of the reaction vial after heating may be dissolved in
 (a) distilled water and added to protein solution. The pH of the solution is adjusted to a desired value by means of a Na$_2$CO$_3$ buffer.
 or
 (b) chloroform for storage of "intermediate" $^{99m}$Tc-complex". Chloroform may be evaporated and procedure a) may be followed as indicated above.
(4) the final reaction mixture obtained according to the procedure mentioned under a) should quietly stand during around 1 hour at room temperature after which the labeling procedure is completed.

The conditions mentioned above lead to a technetium labeling yield of around 95% for HSA and antifibrin.

Utility

This invention is useful for labeling amine-containing compounds, such as proteins, with metals. The labeled proteins are in turn useful in immunodiagnostic/immunotherapeutic applications and other applications.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of labeling an amine-containing substance with a metal, comprising the steps of:

reacting metal ions in an acidic medium with a nitrogen containing compound containing a structure selected from the group consisting of formulas

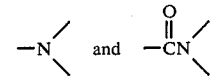

to form a reactive intermediate compound, the amino-containing substances and metal ions being suitable for a diagnostic or therapeutic use, and reacting the reactive intermediate compound with the amine-containing substance to be labeled to provide a metal-labeled amine-containing substance.

2. A method of claim 1, wherein the amine-containing substance is a protein.

3. A method of claim 2, wherein the protein is an antibody.

4. A method of claim 3, wherein the antibody is a monoclonal antibody.

5. A method of claim 1, wherein the nitrogen containing compound is a formamide.

6. A method of claim 5, wherein the formamide is dimethyl formamide.

7. A method of claim 6, wherein dimethyl formamide is reacted with the metal ions at a temperature in the range of from about 135° C. to about 145° C.

8. A method of claim 1, wherein the metal is radioisotope.

9. A method of claim 8, wherein the radioisotope is technetium-99m.

10. A method of claim 6, wherein the metal is a radioisotope.

11. A method of claim 10, wherein the radioisotope is technetium-99m.

12. A method for labeling a monoclonal antibody with technetium-99m ($^{99m}$Tc) metal comprising:
 (a) reacting $^{99m}$Tc-pertechnetate ions with dimethyl formamide under acidic conditions and at an elevated temperature to form a reactive technetium-99m intermediate compound and
 (b) reacting the technetium-99m intermediate compound with a monoclonal antibody to produce a technetium-99m labeled monoclonal antibody.

13. A method of claim 12, wherein the reaction temperature is in the range of form about 135° C. to about 145° C.

* * * * *